United States Patent [19]

Dupriest

[11] Patent Number: 4,968,809

[45] Date of Patent: Nov. 6, 1990

[54] SPIROFLUORENEISOTHIAZOLIDINONE DIOXIDES AS ALDOSE REDUCTASE INHIBITORS

[76] Inventor: Mark T. Dupriest, 3616 Kelvin Ave., Fort Worth, Tex. 76133

[21] Appl. No.: 267,132

[22] Filed: Nov. 4, 1988

[51] Int. Cl.$^5$ .................. A61K 31/425; C07D 275/06
[52] U.S. Cl. ..................................... 548/213; 560/10; 564/84; 564/248; 564/251
[58] Field of Search .................. 548/213, 206, 147

[56] References Cited

U.S. PATENT DOCUMENTS

| | | | |
|---|---|---|---|
| 4,537,892 | 8/1985 | York, Jr. ............................ | 514/278 |
| 4,812,471 | 3/1989 | Schnur ............................... | 514/372 |

OTHER PUBLICATIONS

Burgess, et al., J. Am. Chem. Soc., vol. 95, No. 1, pp. 279–280 (01/10/73).
Burgess, et al., Org. Chem., vol. 39, No. 19, pp. 2885–2892 (1974).

*Primary Examiner*—Diana Rivers
*Attorney, Agent, or Firm*—James Arno; Gregg Brown; Sally Yeager

[57] ABSTRACT

New spirofluoreneisothiazolidinone dioxides and methods for their preparation are disclosed.

8 Claims, No Drawings

SPIROFLUORENEISOTHIAZOLIDINONE DIOXIDES AS ALDOSE REDUCTASE INHIBITORS

FIELD OF THE INVENTION

This invention relates to new and useful spirofluoreneisothiazolidinone dioxides. More particularly, the invention relates to spirofluoreneisothiazolidinone dioxides which are useful as aldose reductase inhibitors.

BACKGROUND OF THE INVENTION

Many compounds and their derivatives have been found to be useful to prevent diabetic cataract, nerve tissue damage and certain vascular changes associated with diabetes mellitus. It is believed that the usefulness of some of these compounds correlates with their observed effect on aldose reductase activity. The inhibition of the enzyme aldose reductase or related enzymes results in the inhibition of abnormal polyol accumulation at the expense of NADPH in those tissues containing aldose reductase and/or related aldehyde reductases. The inhibition of the formation of a polyol such as sorbitol or galactitol, arising from the reduction of an aldose, such as glucose or galactose respectively, is believed to be beneficial in delaying the progression of certain complications arising from hyperglycemia and hypergalactocemia. Hyperglycemia is associated with the complications of neuropathy, nephropathy, retinopathy, cataract, glaucoma and impaired wound healing in persons suffering from diabetes mellitus.

SUMMARY OF THE INVENTION

This invention is directed to spirofluorene-isothiazolidinone dioxides and methods for their preparation.

DETAILED DESCRIPTION OF PREFERRED EMBODIMENTS

The compounds of the present invention are derivatives of spirofluorene- 9,4'- and -9,5'-isothiazolidinone dioxides. These compounds are useful as aldose reductase inhibitors.

The compounds of the present invention have the following general structures.

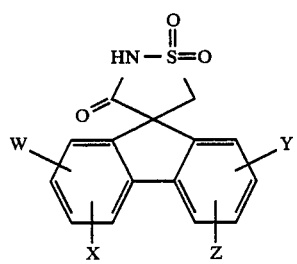

and

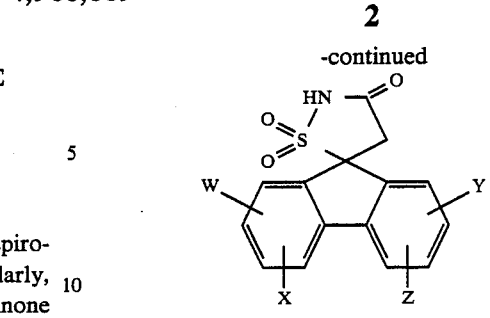

wherein W, X, Y, and Z are selected from: Br, H, F, Cl, lower alkyl sulfide (e.g., —S—CH$_3$), lower alkylsulfinyl (e.g., —S(O)CH$_3$), —OH, CO$_2$R$_1$, lower alkyl, lower alkoxy, lower alkylsulfonyl (e.g., —SO$_2$CH$_3$), —CF$_3$, —S—CF$_3$, —SO$_2$CF$_3$, CO—N(R$_2$)—R$_3$, lower alkyl alcohol (e.g., —CH$_2$—OH), lower alkyl ether (e.g., —CH$_2$OCH$_3$), nitro, lower alkyl sulfide lower alkyl (e.g., —CH$_2$S—CH$_3$), lower alkylamine (e.g. —CH$_2$NH$_2$), lower alkyl esters (e.g., —CH$_2$O—COCH$_3$), carboxylic acids and lower alkyl esters (e.g.,—COOR$_1$), lower alkyl carboxylic acids and esters (e.g.,—CH(CH$_3$)—COOR$_2$) and cycloalkyl of 6 carbon atoms or less (e.g., cyclopropyl);

wherein R$_1$ is lower alkyl (preferably methyl or ethyl); R$_2$ and R$_3$ are selected from the group consisting of H and lower alkyl (preferably methyl or ethyl);

and "lower alkyl" means a moiety with 6 or more atoms.

Compounds of the present invention include pharmaceutically acceptable salts of the above defined structures.

The compounds of structure II are preferred. The preferred compound within structure I is:

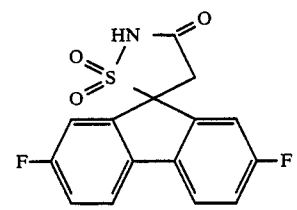

2,7-difluorospiro[9H-fluorene-9,5'-isothiazolidine]-1',1'-dioxide-3'-one

Methods for synthesizing some of the compounds of the present invention are described in the following examples. These examples are meant to be illustrative, but in no way limiting.

EXAMPLE 1

Preparation of Spiro[9H-fluorene-9,4'-isothiazolidine]-1',1'-dioxide-3'-one (3)

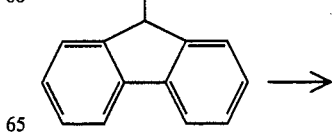

1

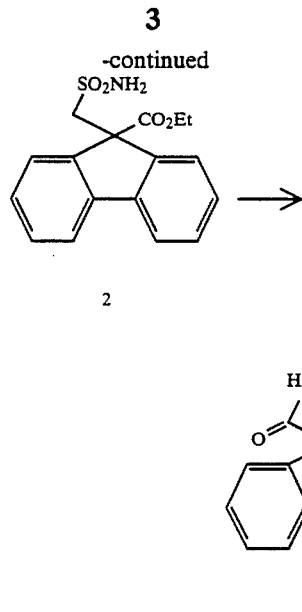

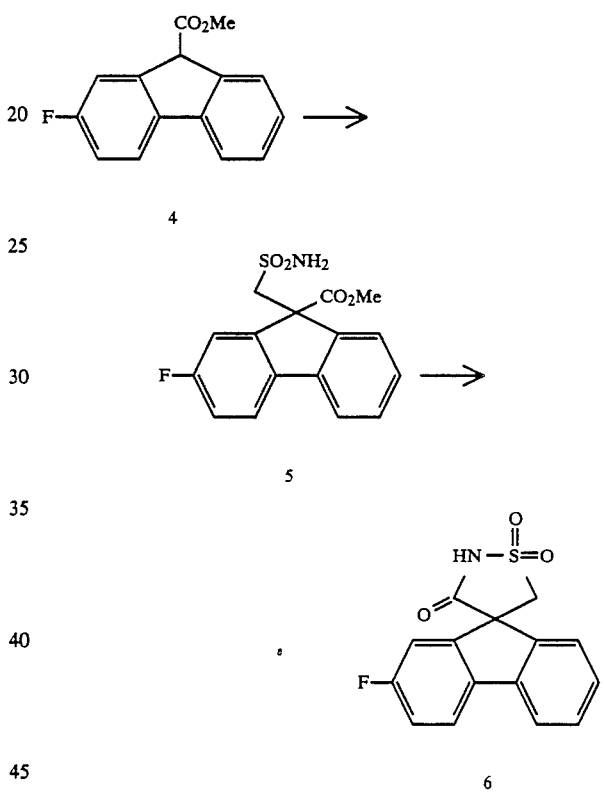

EXPERIMENTAL

Fluorene-9-carboxylic acid ethyl ester (1)

was prepared from commercially available (Aldrich Chemical, Inc.) fluorene-9-carboxylic acid and HCl/EtOH as described in U.S. Pat. No. 4,537,892 (Example VI).

9-Methyl(aminosulfonyl)fluorene-9-carboxylic acid ethyl ester (2)

A mixture of fluorene-9-carboxylic acid ethyl ester (1) (11 g, 46.2 mmoL), potassium carbonate (6.4 g, 46.2 mmoL, 1 eq) and a mixture of bromomethanesulfonamide and iodomethanesulfonamide [prepared from bromomethanesulfonyl chloride see, Trice et al., *J. Org. Chem.*, 32, 990(1967) by reaction with ammonia gas in cold ether followed by reaction with excess sodium iodide in refluxing acetonitrile] (9.1 g, 1 eq) in dry dimethylformamide (100 mL, from sieves) was stirred under nitrogen for 18 h. Water (200 mL) was then added and the solution was acidified with 1N aqueous hydrochloric acid (100 mL) and extracted with ethyl acetate (3×100 mL). The combined organic phases were then washed with brine (3×200 mL), dried (MgSO₄), and concentrated. The residue was purified by column chromatography on silica gel using 40% ethyl acetate in hexane to provide 4.8g (31%) of product (2): mp 150°-156° C.; IR (KBr) 3360, 1710, 740, 725 cm⁻¹; ¹H NMR (CDCl₃, 200 MHz) 7.78-7.69 (m, 4 H), 7.50-7.32 (m, 4 H), 4.38 (bs, 2 H, exchangeable), 4.12 (q. 2 H), 4.11 (s, 2 H), 1.12 (t, 3 H), MS m/z 331 (M+), 178 (base peak).

Spiro[9H-fluorene-9,4,-isothiazolidine]-1',1'-dioxide-3'-one(3)

A mixture of (2) (4 g, 12.1 mmoL) and anhydrous sodium methoxide (4 g) in ethanol (300 mL) was stirred under nitrogen for 1 h at room temperature. The reaction was then evaporated and the residue was acidified with 1N aqueous hydrochloric acid (200 mL) and extracted with ethyl acetate (3×200 mL). The combined organic phases were washed with brine (3×100 mL), dried (MgSO₄), treated with carbon (Norit A), filtered through celite, and concentrated.

The residue was recrystallized twice from methylene chloride/hexane to provide 1 g (30%) of pure product (3): mp 233°-237° C.; IR (KBr) 3200-2600 (broad), 1695 cm⁻¹; ¹H NMR (DMSO-d₆, 200 MHz) 7.93 (m, 2 H), 7.81 (m, 2 H), 7.50 (ddd, 2H, J =1.3, 7.4, 7.4 Hz), 7.40 (ddd, 2 H, J=1.4, 7.4, 7.4 Hz), 4.35 (s, 2 H); MS m/z 285 (M+), 178 (base peak). Anal. calcd. for C₁₅H₁₁NSO₃: C, 63.14; H, 3.89; N, 4.91. Found: C, 63.19; H, 3.98; N, 4.82.

EXAMPLE 2

Preparation of 2-Fluorospiro[9H-fluorene-9,4'-isothiazolidine]-1',1'-dioxide-3'-one (6)

EXPERMENTAL

2-Fluorofluorene-9-carboxylic acid methyl ester (4)

was prepared as described in U.S. Pat. No. 4,537,892 (Example II).

2-Fluoro-9-methyl(aminosulfonyl)fluorene-9-carboxylic acid methyl ester(5)

A mixture of (4) (6.3 g, 26.0 mmoL) and potassium carbonate (3.6 g, 26.0 mmoL, 1 eq) in dry dimethylformamide (200 mL, from CaH₂) was stirred under nitrogen at 40° C. for 30 minutes. Iodomethanesulfonamide [prepared from bromomethanesulfonyl chloride see, Trice et al., *J. Org. Chem.*, 32,990(1967) by reaction with ammonia gas in cold ether followed by reaction with excess sodium iodide in refluxing acetonitrile] (5.7 g, 26.0 mmoL, 1 e.q.) was then added and the reaction was stirred at 40° C. for 6 h and finally at room temperature overnight. The reaction was then diluted with water (200 mL), neutralized with 1N aqueous hydrochloric acid, and extracted with ethyl acetate (3×200 mL). The combined organic phases were washed with brine (3×100 mL), dried (MgSO$_4$), and concentrated. The oily residue was purified by column chromatography on silica gel using 40% ethyl acetate in hexane to provide 2.4 g (27%) of product (5): mp 165°-179° C.; IR (KBr) 3330, 3260, 1735 cm$^{-1}$; $^1$H NMR (CDCl, 200 MHz) 7.74-7.67 (m, 3H), 7.52-7.31 (m, 3H), 7.17 (ddd, 1H, J=2.4, 8.4, 8.9 Hz), 4.49 (bs, 2H, exchangeable), 4.17 (d, 1H, J=14.8Hz), 4.03 (d, 1H, J=14.8Hz), 3.66 (s, 3H); MS m/z 335 (M+), 196 (base peak).

2-Fluorospiro(9H-fluoro-9,4,-isothiazolidine]-1',1'-dioxide-3'-one (6)

A mixture of (5) (2.1 g, 6.2 mmoL) and anhydrous sodium methoxide (1.2 g, 24.8 mmoL, 4 eq) in ethanol (200 mL) was stirred at room temperature under nitrogen for 40 minutes. The reaction was then diluted with water (100 mL), acidified (pH 1) with 5% aqueous hydrochloric acid, and extracted with ethyl acetate (3×200 mL). The combined organic phases were washed with brine (3×100 mL), dried (MgSO$_4$), and concentrated. The residue was recrystallized twice from ethyl acetate/hexane to provide 300 mg (16%) of product (6): mp 263°-270° C.; IR (KBr) 1700, 1330 cm$^{-1}$; $^1$H NMR (DMSO-d$_6$, 200 MHz) 8.00-7.30 (m, 7H), 4.43 (d, 1H, J=14.1Hz), 4.31 (d, 1H, J=14.0Hz); MS m/z 303 (M+), 196 (base peak). Anal. calcd. for C$_{15}$H$_{10}$FNO$_3$S: C, 49.40;H, 3.32; N, 4.62. Found: C, 59.44;H, 3.53; N, 4.59.

EXAMPLE 3

Preparation of Spiro[9H-fluorene-9,5'-isothiazolidine]-1',1'-dioxide-3'-one (10)

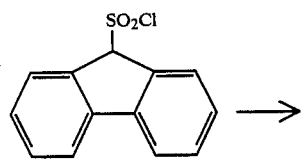

7

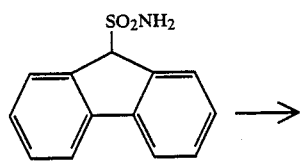

8

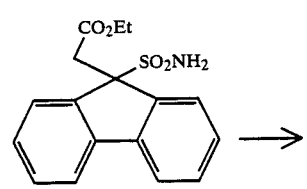

9

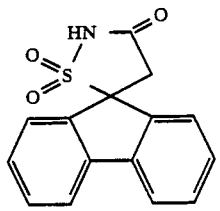

10

EXPERIMENTAL

Fluorene-9-sulfonyl chloride (7)

was prepared from fluorene according to the procedure of Paquette, et al. *J. Org. Chem.*, 34, 2901 (1969).

Fluorene-9-sulfonamide (8)

A solution of (7) (18 g, 68.2 mmoL) in 150 mL of tetrahydrofuran was added over 30 minutes to chilled (−10° C.) tetrahydrofuran (200 mL) through which ammonia gas was bubbling. The reaction was stirred an additional 30 minutes before it was diluted with water (500 mL) and extracted with ethyl acetate (3×150 mL). The combined organics were washed with brine (3×200 mL), dried (MgSO$_4$), filtered and evaporated. The residue was triturated with ether/pet. ether to provide 14.7 g(88%) of product. An analytically pure sample was obtained by chromatography on silica gel eluting with 20% ethyl acetate in petroleum ether: mp 204°-206° C.; IR (KBr) 3360, 3270, 3240, 1320, 735 cm$^{-1}$; $^1$H NMR (DMSO-d$_6$, 270 MHz) 7.97-7.37 (8H, aromatic protons), 5.42 (s, 1H), 3.96 (s, 2H); MS m/z 245 (M+). Anal. calcd. for C$_{13}$H$_{11}$NO$_2$S: C, 63.65;H, 4.52; N, 5.71. Found: C, 63.64;H, 4.59; N, 5.62.

9-(Aminosulfonyl)fluorene-9-acetic acid ethyl ester (9)

To a stirred, 15° C. suspension of sodium hydride (60% in mineral oil, 500 mg, 12.2 mmoL, 1 eq) in 50 mL of dry dimethylformamide (from molecular sieves) under nitrogen was added dropwise over 15 minutes a solution of (8) (3 g, 12.2 mmoL) in 100 mL of dimethylformamide. A solution of ethyl bromoacetate (2.0 g, 12.2 mmoL, 1 eq) in 20 mL of dimethylformamide was then added dropwise over 10 minutes. After 3 h at room temperature, the reaction was diluted with water (100 mL), acidified (pH 5) and extracted with ethyl acetate (3×200 mL). The combined organic extracts were washed with brine (5×100 mL), dried (MgSO$_4$), filtered and evaporated. The crude oil was purified by chromatography on silica gel using a gradient of 10%-30% ethyl acetate in hexane to provide 1 g (25%) of product: mp 167°-170° C., $^1$H NMR (CDCl$_3$) 7.8-7.2 (m, 8H, aromatic protons), 3.9 (broad single, 2H), 3.6 (s, 2H), 3.5 (q, 2H), 1.7 (t, 3H).

Spiro[9H-fluorene-9,5'-isothiazolidine]-1',1'-dioxide-3'-one (10)

A mixture of (9) (85.0 mg, 2.6 mmoL) and anhydrous sodium methoxide (1 g, 7 eq) in methanol was stirred at room temperature for 18 h. The solvent was then evaporated, and the residue was partitioned between water (100 mL) and ethyl acetate (100 mL). The aqueous layer was separated and the organic phase was extracted with 1N aqueous sodium hydroxide (2×100 mL). The combined basic aqueous layers were then washed with ethyl acetate (2×100 mL), acidified with concentrated hydrochloric acid (pH 2) and extracted with ethyl acetate (3×100 mL). The combined organic layers were washed with brine (4×100 mL), dried (MgSO$_4$), filtered and evaporated. The crude solid 600 mg (82%) was recrystallized from ethyl acetate/hexane to provide 200 mg (27%) of pure product 0): mp 236°–239° C.; IR (KBr) 3090 (broad), 2970 (broad), 1710, 1440, 1330 cm$^{-1}$; $^1$H NMR (DMSO-d$_6$, 200 MHz) 7.99–7.45 (m, 9H), 3.64 (s, 2H); MS m/z 285(M+). Anal. calcd. for C$_{15}$H$_{11}$NO$_3$S: C, 63.14; H, 3.89; N, 4.91. Found: C, 62.88; H, 3.94; N, 4.91.

EXAMPLE 4

Preparation of 2-Fluorospiro[9H-fluorene-9,5,-isothiazolidine]-1',1'-dioxide-3'-one (16)

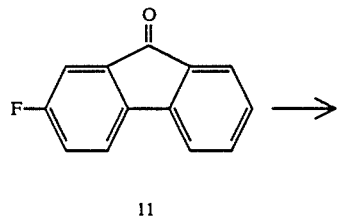

11

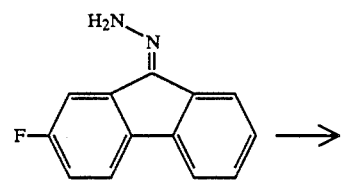

12

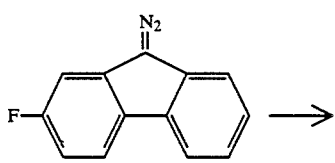

13

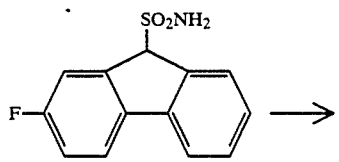

14

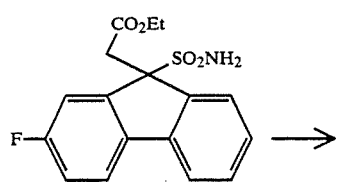

15

-continued

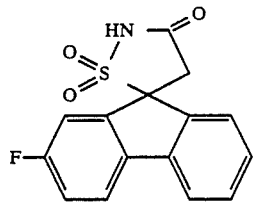

16

EXPERIMENTAL

2-Fluoro-9-fluorenone hydrazone (12)

A mixture of commercially available (Aldrich Chemical, Inc.) 2-fluoro-9-fluorenone (11) (10 g, 50.5 mmoL) and hydrazine monohydrate (10 mL, 200 mmoL, 4 eq) in ethanol (250 mL) was refluxed for 1.5 h. The solution was then reduced in volume (to about a 100 mL) and chilled. The solid that separated was collected by filtration, washing with cold ethanol to provide 6.5 g (60%) of product (12): mp 161°–165° C.; IR (KBr) 3390, 3310, 3200, 1450 cm$^{-1}$; $^1$H NMR (CDCl$_3$, 200 MHz) 7.85 (bd, 1H, J=7.3Hz), 7.69 (bd, 1H, J=7.1Hz), 7.57 (dd, 1H, J=4.8, 8.1Hz), 7.36 (m, 3H), 7.02 (ddd, 1H, J=2.5, 8.3, 9.2Hz), 6.48 (bs, 2H); MS m/z 212 (M+), 183 (base peak).

2-Fluoro-9-diazofluorene (13)

A mixture of (12) (6.5 g, 30.6 mmoL) and activated manganese dioxide (13 g, 150 mmoL, 5 eq) in tetrahydrofuran (300 mL) was stirred at room temperature for 18 h. The reaction was then filtered through celite and concentrated to provide 6.5 g (100%) of product (13) as a red solid which was used without further purification. A sample recrystallized from ether/hexane provided the following data: mp 89°–90 ° C.; IR (KBr) 2075, 1180 cm$^{-1}$; $^1$H NMR (CDCl$_3$, 200 MHz) 7.88–7.79 (m, 2H), 7.49–7.26 (m, 3H), 7.15 (bdd, 1H, J=2.3, 8.9Hz), 7.01 (ddd, 1H, J=2.3, 8.5, 9.3 Hz); MS m/z 210 (M+), 182 (base peak).

2-Fluorofluorene-9-sulfonamide (14)

A mixture of (13) (5.5 g, 26.1 mmoL) in tetrahydrofuran (600 mL) was heated to reflux and treated first with ammonia and then with sulfur dioxide gas a number of times until all of the starting material was consumed by TLC (30% ethyl acetate in hexane). After solvent removal, the residue was diluted with water (200 mL) and extracted with ethyl acetate (3×200 mL). The combined organic extracts were dried (MgSO$_4$), concentrated, and chromatographed on silica gel using 20% ethyl acetate in hexane to provide 5 g(73%) of product: mp 179°–181° C.; IR (KBr) 3390 (broad), 3280, 1322 cm$^{-1}$; $^1$H NMR (CDCl$_3$, 200 MHz) and 7.95–7.16 (m, 7H), 5.37 (s, 1H), 4.00 (bs, 2H); MS m/z 263 (M+), 183 (base peak).

9-(Aminosulfonyl)-2-fluorofluorene-9-acetic acid ethyl ester (15)

Under nitrogen (14) (3.0 g, 11.4 mmoL) was added portionwise to a stirred suspension of sodium hydride (570 mg of 60% dispersion in mineral oil, 1.25 eq) in 200 mL of dry dimethylformamide (from sieves). After 20 min, ethyl bromoacetate (1.58 mL, 1.25 eq) was added and the mixture was stirred for an additional hour before it was diluted with water (300 mL) and extracted with ethyl acetate (3×200 mL). The combined organics were washed with brine (5×200 mL), dried (MgSO₄) and concentrated. The residue was recrystallized from ethyl acetate/hexane to provide 2.2 g(56%) of product (15): mp 186°–187° C.; IR (KBr) 3350, 3250, 1710, 1158 cm⁻¹; ¹H NMR (CDCl₃, 200 MHz) 7.81–7.67 (m, 3H), 7.55–7.32 (m, 3H), 7.19 (ddd, 1H, $J=2.4, 8.7, 8.7Hz$), 3.93 (bs, 2H, exchangeable), 3.71 (q, 2H, $J=7.1Hz$), 3.68 (s, 2H), 0.78 (t, 3H, $J=7.1Hz$); MS m/z 349 (M+), 197 (base peak).

2-Fluorospiro[9H-fluorene-9,5′-isothiazolidine]-1′,1′-dioxide-3′-one (16)

A mixture of (15) (1.2 g, 3.4 mmoL) and sodium hydride (1.3 g of a 60% dispersion in mineral oil, 9.5 eq) in dry tetrahydrofuran (300 mL, from CaH₂) was stirred at room temperature under nitrogen for 30 min. The mixture was then diluted with 1N aqueous hydrochloric acid (200 mL) and extracted with ethyl acetate (3×150 mL). The combined organic extracts were washed with brine (100 mL) dried (MgSO₄) and concentrated. The residue was first leached with ether/hexane and then recrystallized from ethyl acetate/hexane to provide 500 mg (55%) of product (16) as a white solid: mp 259°–265° C. (dec); IR (KBr) 1695, 1320 cm⁻¹, ¹H NMR (DMSO-d₆, 200 MHz) 11.7 (b, 1H, exchangeable), 8.04 7.93 (m, 2H), 7.66–7.37 (m, 5H), 3.81 (d, 1 H, $J=17.5Hz$), 3.55 (d, 1H, $J=17.5Hz$); MS m/z 303 (M+), 196 (base peak). Anal. calcd. for $C_{15}H_{10}FNO_3S$: C, 59.40;H, 3.32; N, 4.62. Found: C, 59.30;H, 3.33; N, 4.62.

EXAMPLE 5

Preparation of 2-Chlorospiro[9H-fluorene-9,5′-isothiazolidine]-1′,1′-dioxide-3′-one (23)

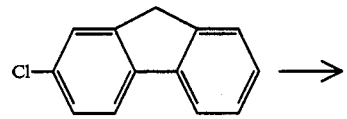

17

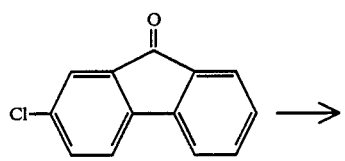

18

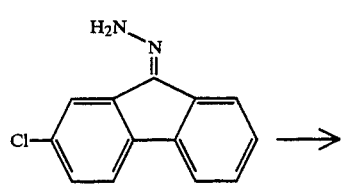

19

-continued

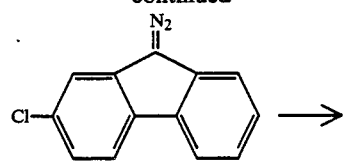

20

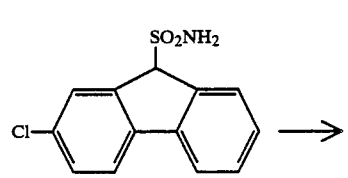

21

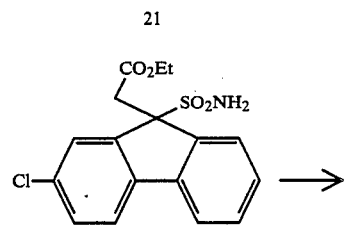

22

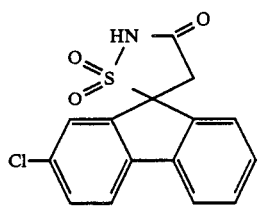

23

EXPERIMENTAL 2-Chloro-9-fluorenone (18)

A methanol free, 40% solution of Triton B in pyridine (8 mL) was added to a stirred, room temperature solution of commercially available (Alpha) 2-chlorofluorene (17) (42 g, 0.21 mmoL) in pyridine (257 mL) and oxygen was bubbled through the mixture at a moderate rate for 18 h. The majority of the pyridine was then removed on the rotary evaporator at reduced pressure and 5% aqueous hydrochloric acid (500 mL) was added to the residue. The solid was collected by filtration and washed with 5% aqueous hydrochloric acid and water. After drying, the solid was extracted repeatedly with hexane to remove some hexane insoluble impurities. Evaporation of the hexane left 42.7 g(95%) of 2-chloro-9-fluorenone: mp 110°–113° C.

2-Chloro-9-fluorenone hydrazone (19)

A mixture of 2-chloro 9-fluorenone (18) (5 g, 23.3 mmoL), hydrazine monohydrate (6 mL, 120 mmoL, 5.2 eq) and acetic acid (1 mL) in ethanol (150 mL ) was refluxed for 2.5 h. The mixture was then evaporated to dryness to provide 5.3 g (100%) of product which was used without further purification: mp 139°–143° C..

2-Chloro-9-diazofluorene (20)

A mixture of (19) (5.3 g, 23.2 mmoL) and activated manganese dioxide (20 g, 232.5 mmoL, 10 eq) in tetrahydrofuran (500 mL) was stirred at room temperature for 18 h. The mixture was then filtered through celite and concentrated to provide 5.3 g (100%) of product (20) as a red solid: mp 102°–108° C.

2-Chlorofluorene-9-sulfonamide (21)

A mixture of (20) (5.3 g, 23.4 mmoL) in tetrahydrofuran was alternately treated with ammonia and sulfur dioxide gas a number of times until TLC (30% EtOAC/hexane) indicated that the starting material had been consumed. The reaction was then concentrated and the residue was diluted with water (200 mL) and extracted with ethyl acetate (3×200 mL). The combined organic phases were washed with brine (3×100 mL), dried (MgSO$_4$), and concentrated. The crude solid was recrystallized from ethyl acetate/hexane to provide 3.1 (47%) of product (21): mp 190°–194° C.

9-(Aminosulfonyl)-2-chlorofluorene-9-acetic acid ethyl ester (22)

Under nitrogen, (21) (2.6 g, 9.3 mmoL) was added portionwise to a stirred suspension of sodium hydride (465 mg of a 60% mineral oil dispersion, 1.25 eq) in dry dimethylformamide (60 mL, from CaH$_2$). After 30 minutes, ethyl bromoacetate (1.3 g, 11.6mmoL, 1.25 eq) was added and stirring was continued overnight. The reaction was then diluted with water (200 mL), neutralized, and extracted with ethyl acetate (3×200 mL). The combined organic phases were washed with brine (3×200 mL), dried (MgSO$_4$), and concentrated. The crude solid was recrystallized twice from ethyl acetate/hexane to provide 1.7 g(50%) of product (22): mp 189°–191° C.

2—Chlorosoiro[9H-fluorene-9,5,-isothiazolidine]-1′,1′-dioxide-3′-one (23)

A mixture of (22) (700 mg, 1.91 mmoL) and sodium hydride (230 mg of a 60% mineral oil dispersion, 3 eq) in dry tetrahydrofuran (400 mL, from CaH$_2$) was stirred under nitrogen at 10 ° C. for 1.5 h. The reaction was then evaporated and the residue partitioned between 1N aqueous sodium hydroxide (100 mL) and ethyl acetate (100 mL). The basic aqueous was separated and the organic layer was extracted with 1N aqueous sodium hydroxide (3×200 mL). The combined basic aqueous extracts were acidified (pH 1) with concentrated hydrochloric acid and extracted with ethyl acetate (3×100 mL). The combined organic phases were washed with brine (3×20 mL ), dried (MgSO$_4$), and concentrated to provide 500 mg of solid which was recrystallized from ethyl acetate/hexane to provide 170 mg (27%) of pure product (23): mp 246–248° C.

EXAMPLE 6

Preparation of 2,7-Difluorospiro[9H-fluorene-9,5′-isothiazolidine]-1′,1′-dioxide-3,-one (28)

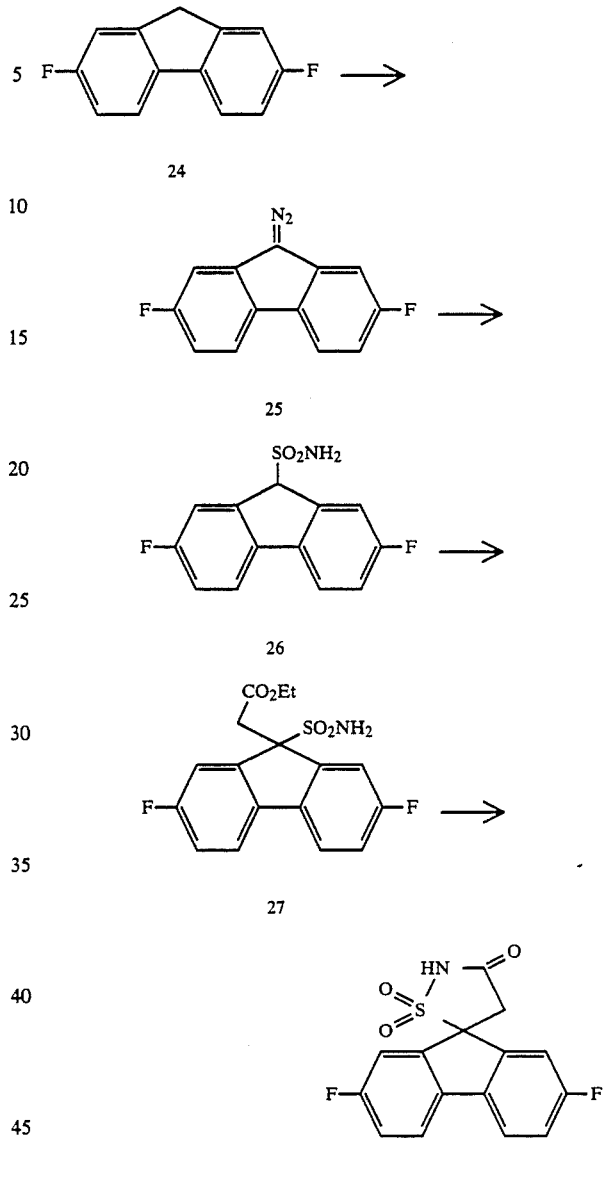

2,7-Difluoro-9-diazofluorene (25)

Under nitrogen, n-butyllithium (20 mL of a 2.5M solution in hexane, 1 eq) was added dropwise to a stirred, −20 ° C. solution of commercially available (Alfred Bader Library of Rare Chemicals) 2,7-difluorofluorene (24) (10 g, 49.5 mmoL) [which may also be prepared according to U.S. Pat. No. 4,436,745] in 250 mL of anhydrous ether. After 10 min., this mixture was transferred via a cannula using nitrogen pressure into a 0° C. solution of p-toluenesulfonylazide [prepared by the method described in Doering, et al. J. Am. Chem. Soc. (1953) 75, 5955] in 200 mL of anhydrous ether over 20 min. The reaction was allowed to warm to room temperature over 1.5 h and was then acidified with 1N aqueous hydrochloric acid and extracted with ethyl acetate (3×200 mL). The combined organics were washed with brine (3×100 mL), dried (MgSO$_4$), and concentrated to provide 10 g of crude material which was leached with ether/hexane to provide 4 g (37%) of product (25): mp 148°–150 °C.; IR (KBr) 2070, 1600, 1575, 845 cm$^{-1}$; $^1$H NMR (CDCl$_3$, 200 MHz) 7.77 (ddd, 2H, J=0.5, 5.0, 8.7Hz), 7.14 (ddd, 2H, J=0.5, 2.5, 8.5Hz), 7.0 (ddd, 2H, J=2.3, 8.5, 9.3Hz); MS m/z 228 (M+), 200 (base peak). Anal. Calcd. for C$_{13}$H$_6$N$_2$F$_2$: C, 68.42;H, 2.65; N, 12.28. Found: C, 68.25;H, 2.78; N, 12.50.

2,7-Difluorofluorene-9-sulfonamide (26)

A mixture of (25) (3.5 g, 15.3 mmoL) in refluxing tetrahydrofuran was treated first with ammonia and then sulfur dioxide gas a number of times until the starting material was consumed (as indicated by TLC using 30% ethyl acetate in hexane). The reaction was then diluted with water (400 mL) and extracted with ethyl acetate (3×100 mL). The combined organic extracts were washed with brine (3×200 mL), dried (MgSO$_4$), and concentrated to provide 4 g of crude material which was chromatographed on silica gel using 25% ethyl acetate in hexane to provide 2.75 g(64%) of product (26): mp 234°–237° C.; IR (KBr) 3417, 3265, 2885, 1575, 805 cm$^{-1}$; $^1$H NMR (CDCl$_3$, 200 MHz) 7.67 (m, 4H), 7.18 (m, 1H), 5.36 (s, 1H), 4.02 (bs, 2H, exchangeable); MS m/z 281 (M+), 201 (base peak). Anal. calcd. for C$_{13}$H$_9$NF$_2$SO$_2$: C, 55.51;H, 3.23; N, 4.98. Found: C, 55.25;H, 3.55; N, 4.63.

9-(Aminosulfonyl)-2.7-difluorofluorene-9-acetic acid ethyl ester (27)

Under nitrogen, (26) (2.4 g, 8.5 mmoL) was added portionwise to a stirred suspension of sodium hydride (427 mg of a 60% dispersion in mineral oil, 1.25 eq) in dry dimethylformamide (60 mL, from CaH$_2$). After 15 min, ethyl bromoacetate (1.8 g, 10.0 mmoL, 1.25 eq) was added and the mixture was stirred for an additional hour before it was diluted with water (200 mL) and extracted with ethyl acetate (3×100 mL). The combined organic extracts were washed with brine (3×200 mL), dried (MgSO$_4$), and concentrated. The residue was recrystallized from ethyl acetate/hexane to provide 1.5 g. A sample recrystallized a second time from ethyl acetate/hexane provided the following data: mp 215°–217° C.; IR (KBr) 3357, 3250, 1710, 1160, 828 cm$^{-1}$; $^1$H NMR (CDCl$_3$, 200 MHz) 7.65 (dd, 2H, J=4.8, 8.6Hz), 7.52 (ddd, 2 H, J=2.5, 9.3Hz), 7.20 (ddd, 2H, J=2.3, 8.6, 8.6Hz), 3.97 (bs, 2H, exchangeable), 3.75 (q, 2H, J=7.1H), 0.85 (t, 3H, J=7.1Hz); MS m/z 367 (M+), 215 (base peak).

2,7-Difluorospiro[9H-fluorene-9,5'-isothiazolidine]-1',1'-dioxide-3'-one (28)

A mixture of (27) (1.1 g, 3.0 mmoL) and sodium hydride (1.2 g of a 60% dispersion in mineral oil, 10 eq) in dry tetrahydrofuran (300 mL, from CaH$_2$) was stirred at room temperature under nitrogen for 45 min. The reaction was then partitioned between water (100 mL) and ether, the basic aqueous was separated, and the organic phase was extracted with 1N aqueous sodium hydroxide (3×75 mL). The combined basic aqueous extracts were then washed with ether (3×100 mL), acidified with concentrated hydrochloric acid, and extracted with ethyl acetate (3×100 mL). The combined organic phases were then washed with brine (100 mL), dried (MgSO$_4$), and concentrated. The residue was chromatographed on silica gel using 10% methanol in methylene chloride to provide 750 mg of solid which was recrystallized from ethyl acetate/hexane to provide 290 mg (30%) of pure product (28): mp 259°–262° C.; IR (KBr) 3280-2900 (broad), 1730, 1710, 1157, 815 cm$^{-1}$; $^1$H NMR (DMSO-d$_6$, 200 MHz) 7.99 (dd, 2H, J=4.9, 8.5Hz), 7.47 (m, 4H), 3.72 (s, 2H); MS m/z 321 (M+), 214 (base peak). Anal. Calcd. for C$_{15}$H$_9$F$_2$NO$_3$S: C, 56.07;H, 2.82; N, 4.36. Found: C, 55.96;H, 3.01; N, 4.31.

We claim:

1. A compound of the formula:

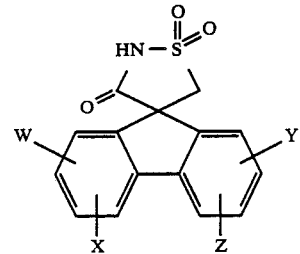

and pharmaceutically acceptable salts thereof wherein W, X, Y and Z are selected from:

Br, H, F, Cl, lower alkyl sulfide, lower alkylsulfinyl, —OH, CO$_2$R$_1$, lower alkyl, lower alkoxy, lower alkylsulfonyl,—CF$_3$, —S—CF$_3$, —SO$_2$CF$_3$, CO—N(R$_2$)-R$_3$, lower alkyl alcohol, lower alkyl ether, nitro, lower alkyl sulfide lower alkyl, lower alkylamine, lower alkyl esters, —COOH and lower alkyl esters, lower alkyl carboxylic acids and esters and cycloalkyl of 6 carbon atoms or less;

wherein R$_1$ is lower alkyl; and R$_2$ and R$_3$ are selected from the group consisting of H and lower alkyl.

2. A compound according to claim 1 of the formula:

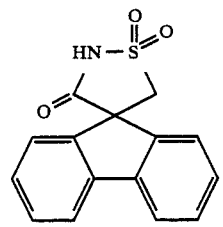

3. A compound according to claim 1 of the formula:

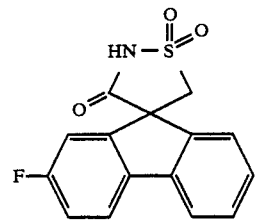

4. A compound of the formula:

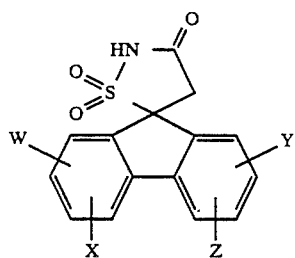

and pharmaceutically acceptable salts thereof wherein W, X, Y and Z are selected from:

Br, H, F, Cl, lower alkyl sulfide, lower alkylsulfinyl, —OH, $CO_2R_1$, lower alkyl, lower alkoxy, lower alkylsulfonyl, —$CF_3$, —S—$CF_3$, —$SO_2CF_3$, CO—$N(R_2)$-$R_3$, lower alkyl alcohol, lower alkyl ether, nitro, lower alkyl sulfide lower alkyl, lower alkylamine, lower alkyl esters, —COOH and lower alkyl esters, lower alkyl carboxylic acids and esters and cycloalkyl of 6 carbon atoms or less;

wherein $R_1$ is lower alkyl; and $R_2$ and $R_3$ are selected from the group consisting of H and lower alkyl.

5. A compound according to claim 4 of the formula:

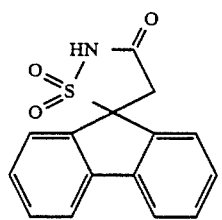

6. A compound according to claim 4 of the formula:

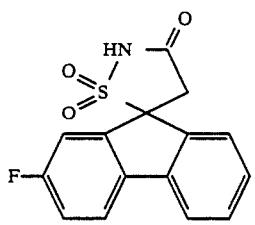

7. A compound according to claim 4 of the formula:

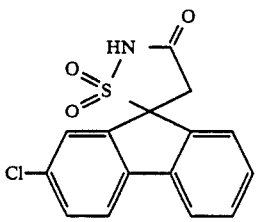

8. A compound according to claim 4 of the formula:

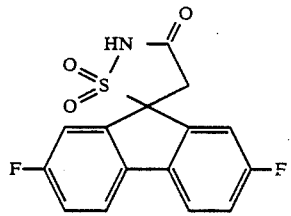

* * * * *